US010238166B2

(12) United States Patent
Rosenbaum

(10) Patent No.: US 10,238,166 B2
(45) Date of Patent: Mar. 26, 2019

(54) INSTRUMENTED ARTICLE OF FITNESS AND METHOD OF DETERMINING CALORIC REQUIREMENTS

(76) Inventor: Robert Rosenbaum, Gaithersburg, MD (US)

( * ) Notice: Subject to any disclaimer, the term of this patent is extended or adjusted under 35 U.S.C. 154(b) by 0 days.

(21) Appl. No.: 13/536,876

(22) Filed: Jun. 28, 2012

(65) Prior Publication Data
US 2013/0005534 A1 Jan. 3, 2013

Related U.S. Application Data

(60) Provisional application No. 61/502,131, filed on Jun. 28, 2011.

(51) Int. Cl.
A43B 3/00 (2006.01)
A61B 5/00 (2006.01)
A61B 5/11 (2006.01)

(52) U.S. Cl.
CPC .......... *A43B 3/0015* (2013.01); *A61B 5/1118* (2013.01); *A61B 5/6825* (2013.01); *A61B 5/6829* (2013.01); *A61B 2562/0252* (2013.01)

(58) Field of Classification Search
CPC . A63B 24/00; A63B 24/0003; A63B 24/0062; A61B 5/1118; A61B 5/6825; A61B 2562/0252; A61B 2562/0219
USPC ................................................ 482/1, 8, 900
See application file for complete search history.

(56) References Cited

U.S. PATENT DOCUMENTS

| 4,233,477 | A | 11/1980 | Rice |
| 4,867,442 | A | 9/1989 | Matthews |
| 5,336,959 | A | 8/1994 | Park |
| 5,974,898 | A | 11/1999 | Golderer |
| 6,790,178 | B1 | 9/2004 | Mault |
| 6,925,851 | B2 | 8/2005 | Reinbold |
| 7,118,990 | B1 | 10/2006 | Xu |
| 7,367,242 | B2 | 5/2008 | Xi |
| 8,287,434 | B2 * | 10/2012 | Zavadsky et al. ................ 482/5 |
| 2002/0086774 | A1 * | 7/2002 | Warner ............................ 482/8 |
| 2006/0047447 | A1 | 3/2006 | Brady |
| 2007/0068244 | A1 | 3/2007 | Billing |
| 2008/0204225 | A1 | 8/2008 | Kitchen |
| 2009/0048070 | A1 * | 2/2009 | Vincent et al. .................. 482/8 |
| 2011/0112771 | A1 * | 5/2011 | French .......................... 702/19 |
| 2011/0306471 | A1 * | 12/2011 | Huang ........................... 482/44 |

(Continued)

Primary Examiner — Sundhara M Ganesan
(74) Attorney, Agent, or Firm — Global Intellectual Property Agency, LLC; Daniel Boudwin

(57) ABSTRACT

Disclosed is a force measuring article of athletic equipment and method of monitoring caloric output during a physical exercise. Force transducers are positioned within the palm region of a lifting glove or sole portion of an athletic shoe for measuring force versus time data and storing the data for later retrieval and analysis. The force output for a given exercise is analyzed such that the user is able to monitor and gauge energy output during an activity without the use of a heart rate monitor or larger, external equipment. The data can be used to determine caloric output, from which the user can directly measure the energy required for a specific exercise and the necessary calories required to complete the exercise. The method involves gather this information and using it as means to further understand caloric output, and thus meter caloric intake and maintain a proper daily caloric balance.

7 Claims, 2 Drawing Sheets

(56) References Cited

U.S. PATENT DOCUMENTS

2012/0041767 A1* 2/2012 Hoffman ............ A63B 24/0059
                                                                             705/1.1
2012/0136231 A1* 5/2012 Markel ........................ 600/388
2012/0139731 A1* 6/2012 Razoumov et al. ....... 340/573.1

* cited by examiner

INSTRUMENTED ARTICLE OF FITNESS AND METHOD OF DETERMINING CALORIC REQUIREMENTS

CROSS REFERENCE TO RELATED APPLICATION

This application claims the benefit of U.S. Provisional Application No. 61/502,131 filed on Jun. 28, 2011, entitled "Energy Devices." The patent application identified above is incorporated here by reference in its entirety to provide continuity of disclosure.

BACKGROUND OF THE INVENTION

Field of the Invention

The present invention relates to instrumented lifting equipment and means for data acquisition during physical exercise. More specifically, the present invention pertains to an article of fitness that involves force measurements recorded by sensors imbedded within the article for calculating input on the human body, using the collected data to analyze the exercise and to determine caloric output based on recorded metrics.

Many individuals are not aware of their daily caloric balance, which compares the energy of food taken into the body versus the energy expended over the course of the day. This balance is critical for maintaining a desired weight, remaining physically fit and maintaining overall good health. Calories taken in by food and beverages are utilized for bodily function and for operating muscles when the body transforms and expends that energy in the form of mechanical work. This work includes daily activities and extends to periods of exercise when higher caloric output levels are required. Those individuals looking to lose weight tend to expend more than they consume, while those looking to maintain a given weight will keep an even input/output balance. Those excess and under utilizing calories are typically stored as fat in the body, therefore proper balance and monitoring of caloric input versus output is necessary for a balanced lifestyle and healthy maintenance of weight.

For those individuals seeking to gain muscle mass or to strengthen their body, maintaining caloric balance is critical, as these individuals tend to require a larger intake of calories to offset their high caloric output (in the form of weight training and high intensity exercise). Users expend considerable amounts of energy through weight lifting, fitness training and other body movements. However, the exact caloric output of a specific exercise or activity may not be readily known to the user, and may only be measurable through cardiac measurements that monitor the user's heart rate and correlate the readings to empirical data for caloric burn based on the user's body type. This type of calculation is based on averages, wherein a heart rate monitor is utilized to measure heart rate and determines an approximate caloric burn rate. This measurement, however, is not well adapted for anaerobic exercises that do not involve increased heart rates. Specifically, those users engaging in weight training activities may not be aware or have a means of measuring the force and energy expelled during a particular exercise, which may then be utilized to measure caloric output of the specific exercise for the purposes of maintaining a proper caloric balance. Weight lifters therefore do not know the true caloric expenditure of an exercise, while runners do not know the true caloric expenditure of a run without using empirical formulas. Not knowing the actual force applied to or by the human body can make it difficult to assess one's workouts. In addition, it is helpful to know the actual energy that should be avoided in order to prevent an injury in certain activities and events.

The present invention relates to a means of measuring force and impulse data from within an article of exercise equipment. Preferably, weight lifting gloves and the soles of shoes are utilized as structures within which piezoelectric sensors capture measured forced over a desired time interval. During this period, a force versus time chart is developed, from which certain metrics may be derived that provide the user with tangible data from which to calculate caloric output, monitor the input of a given exercise on the body, and to further adjust caloric intake levels as desired. This measured data provides a means to directly calculate the energy and force required by the user to complete the exercise, and does not rely on empirical or averaged data as a means to determine caloric output and the energy required for a specific exercise or activity.

Description of the Prior Art

Devices have been disclosed in the prior art that relate to force measurements and instrumented athletic equipment. These include devices that have been patented and published in patent application publications, and generally relate to larger monitoring devices, instrumented boxing gloves and measuring impact forces between athletes. The forgoing is a list of devices deemed most relevant to the present disclosure, which are herein described for the purposes of highlighting and differentiating the unique aspects of the present invention, and further highlighting the drawbacks existing in the prior art.

Specifically, U.S. Pat. No. 4,867,442 to Matthews discloses an exercise aid head band that comprises a microprocessor to process heart rate, time and exercise related inputs for recordation and tracking. The device incorporates voice synthesizer for outputting directions and information to the user, whereafter the device is connectable to a computer for downloading and uploading information and for further data analysis. The device is adapted to track user performance and to aid a user maintaining an optimum heart rate throughout an aerobic exercise. The device monitors user output in the form of heart rate, which can provide data from which overall work and caloric output has been achieved during an exercise routine. The present invention, alternatively, provides a direct measurement of load entering from a given load path for determining and tracking input on the human body during lifting exercises or during an impact event.

U.S. Pat. No. 6,790,178 to Mault discloses a physiological monitor module for use with a personal digital assistant (PDA), which is used to record and track data from various modules attached thereto, as well as provide an interface for interpreting, displaying or transferring data to a personal computer. One or more sensors are attached to the PDA for monitoring a given variable during an exercise, wherein the PDA provides a means to store, process and further transfer the information after the exercise related to the signals received from the attached sensor. Several embodiments are disclosed for this general purpose, wherein different sensors and PDA capabilities are highlighted. The use of a PDA provides a novel and flexible means of reading sensor date, wherein the sensor is easily replaced or updated for the tracking of different variables; however the device differs significantly in design elements from the present invention, which is related to imbedded sensors in equipment or clothing for recording and storing load input onto the human body.

U.S. Published Patent Application Publication No. 2007/0068244 to Billing discloses a system for measuring ground reaction force and analyzing performance of a user, wherein a three dimensional accelerometer and force sensors in the user's shoes are utilized to derive the three components of the ground reaction force. The accelerometer is positioned on the user's torso and in proximity to his or her center of gravity, while wireless communication allows connection of the accelerometer with the force sensors in each shoe. Contact time, frequency, and force amplitude in conjunction with the directional calculation measuring means of the accelerometer are utilized to calculate all components of the ground reaction force on the user. The Billing disclosure is related to user performance and measuring ground reaction force while running, which can be utilized characterize the efficiency of the athletic movements. This device is related to running kinematics and the effectiveness of a user's stride, as opposed to a device that monitors force output while exercising for the purposes of caloric balance monitoring and determining the output of a user during a lifting exercise.

U.S. Pat. No. 6,925,851 to Reinbold discloses a method and system for detecting and displaying impacts received on a piece of athletic equipment having two or more items of equipment having a force sensor, logic and wireless transmitter therein. A receiver and processor accepts the signals from the transmitter for reading and cataloging the sensor data, which the athletic equipment is preferably boxing gloves for measuring impact force between competitors in a boxing match. A computer is utilized to interpret and display impact information, while the logic and receiver are adapted to allow recordation of each impact and its impact load. This allows the number of blows and their intensity during a fighting match, which can be used during a match to determine who has an advantage and who is leading the match during a prolonged battle in which judges are utilized to determine the victor.

U.S. Published Patent Application Publication No. 2008/0204225 to Kitchen discloses a system for recording force and motion data from a user during a physical workout, wherein the motion of the user is captured, collected and analyzed for providing feedback to the user engaged in weight lifting or physical rehabilitation exercises. A data collection device on the user and in wireless communication with motion-sensing devices records data that can later be uploaded onto a base computing device for analysis. The analysis of the user's motion provides insight into the effectiveness of the workout and the user's performance. The Kitchen device, while disclosing a similar exercise device, is particularly related to user motion during an exercise, rather than energy output for caloric balance considerations.

The present invention provides a means to directly measure the force being applied to a user's body during an exercise or activity, wherein piezoelectric force transducers and suitable data storage means are placed within an article of athletic equipment for calculating force over time through the article of equipment. Specifically contemplated are a pair of lifting gloves and a pair of shoes, wherein the palm region of the gloves and the soles of the shoes include the force transducers. Just prior to an exercise, the device may be initiated to begin data collection, after which the device may be deactivated. The stored force-time history data is stored within the memory, after which it can be uploaded onto a computer interface for performance tracking and analysis. The results of the data determine the energy expelled by the user during the exercise and thus the caloric requirements therefore. This can be used for maintaining a proper caloric balance, tracking performance and determining the energy output for a specific exercise. It is submitted that the present invention is substantially divergent in design elements from the prior art, and consequently it is clear that there is a need in the art for an improvement to existing energy usage monitor devices. In this regard the instant invention substantially fulfills these needs.

SUMMARY OF THE INVENTION

In view of the foregoing disadvantages inherent in the known types of instrumented exercise equipment now present in the prior art, the present invention provides a new energy measuring article of athletic equipment, wherein the same can be utilized for providing convenience for the user when monitoring force and energy output during a given exercise or lift, and analyzing energy output for maintaining a healthy daily caloric balance and monitoring the intensity of a specific workout.

It is therefore an object of the present invention to provide a new and improved force and energy measuring device and method that has all of the advantages of the prior art and none of the disadvantages.

It is another object of the present invention to provide an imbedded force transducer into a lifting glove or running shoe for measuring force over a period of time, wherein the data is stored within an imbedded computer storage means for later downloading and analysis.

Another object of the present invention is to provide a method of determining caloric output for a specific exercise using force transducers within hand or foot athletic apparel, and utilizing this data for determining energy output required for the given exercise and the necessary calories therefor.

Yet another object of the present invention is to provide a means and method of monitoring caloric output for a given exercise or activity for the purposes of maintaining a proper daily caloric balance.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
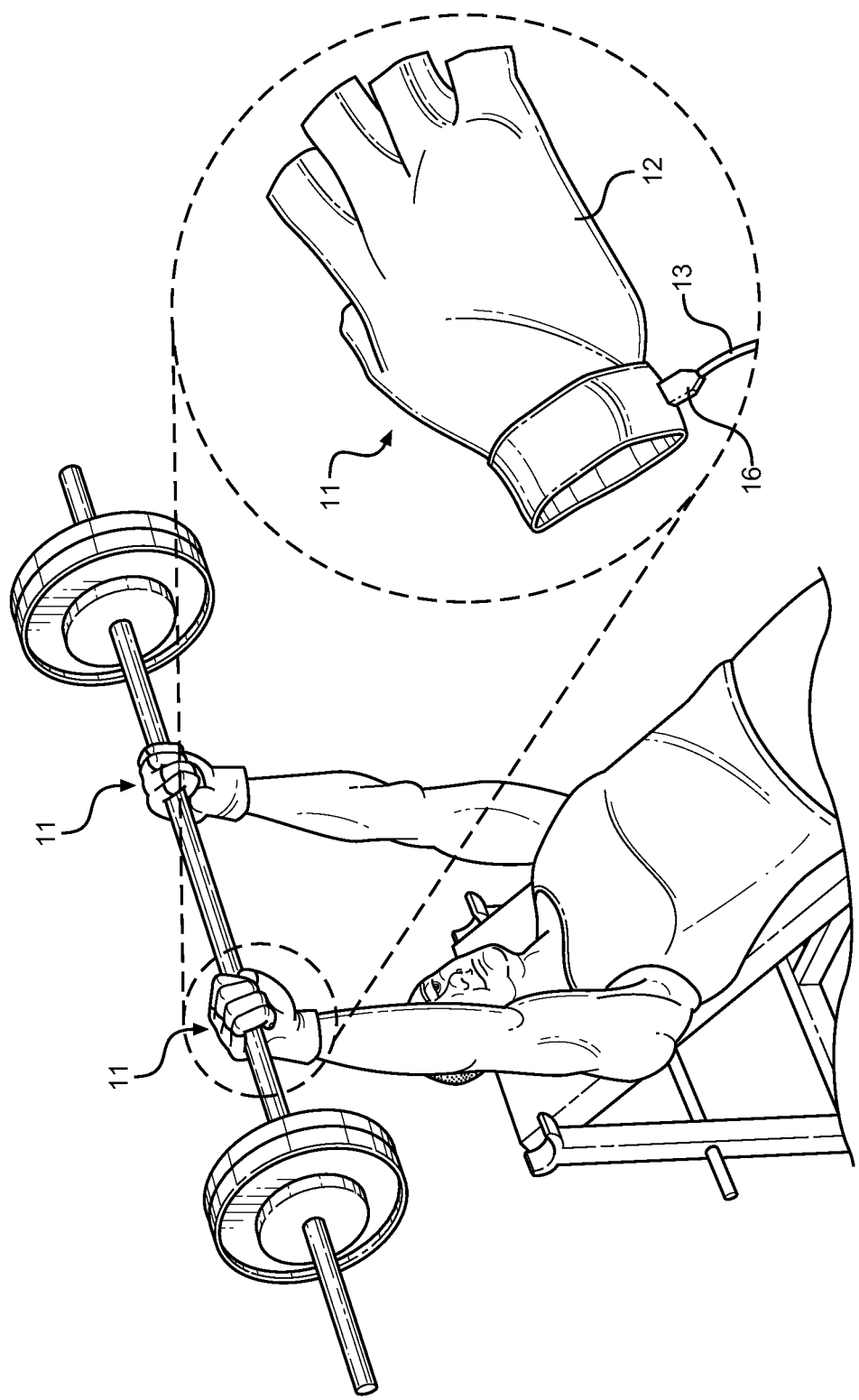
FIG. 1 shows a perspective view of the present device in a working position, monitoring force exerted onto the palm regions of the user during a lifting motion.

Reference is made herein to the attached drawings. Like reference numerals are used throughout the drawings to depict like or similar elements of the energy measuring article of athletic equipment and method of monitoring caloric output. For the purposes of presenting a brief and clear description of the present invention, the preferred embodiment will be discussed as used for measuring force and energy output for a given exercise or activity and utilizing the collected data as a means to determine the activity intensity and caloric requirements. The figures are intended for representative purposes only and should not be considered to be limiting in any respect.

Referring now to FIG. 1, there is shown a view of the present invention in use collecting data while a user is engaging in a lifting exercise. The present invention includes an apparatus for measuring and collecting force data related to physical exercise, along with an associated method of use that includes the deployment of imbedded sensors for collecting force data, wherein the data may be used as a way of calculating actual force output and caloric requirements of an exercise. Energy is expelled during physical activity, wherein energy is transformed into mechanical work by the user displacing an object a given distance. The required force output from the user can be difficult to measure directly, as most typical means of measurement are indirect and related to heart rate. The present invention comprises an article of exercise equipment having an imbedded force transducer and accelerometer that tracks the force output and the movement of the article during an exercise, which can be manipulated to determine the force exerted over a time period and over a distance for the calculation of impulse and work output. The mechanical work during an exercise, or the change in initial and final kinetic energies, equals the caloric output and thus the energy requirement for the given exercise. This measurement can then be utilized to chart caloric output of anaerobic activities such as a weight lifting and similar physical exercise activities that are traditionally difficult to measure and calculate caloric requirements. The force and impulse data can be utilized to determine the impact loads on specific parts of the human body during an activity.

In a specific embodiment, the present invention comprises a pair of lifting gloves 11 that comprise a palm area 12 having at least one imbedded piezoelectric force transducer and an accelerometer for position, velocity and acceleration tracking. Further imbedded within the glove 11 is a computer memory or data storage means, which stores the collected force and acceleration data collected over a given interval. The gloves 11 may further include a means of activation and deactivation, such that data acquisition is not continuous and can be broken into smaller segments for data size management. Along a portion of the gloves is a data transfer means, wherein a connector 16 and cord 13 connect the gloves to a computer workstation for visualization and analysis after an exercise routine. In an alternate configuration, a means of wireless data transfer may be utilized in lieu of a physical connection, reducing the need for a physical connector receptacle on the exercise article.

Figure 2:
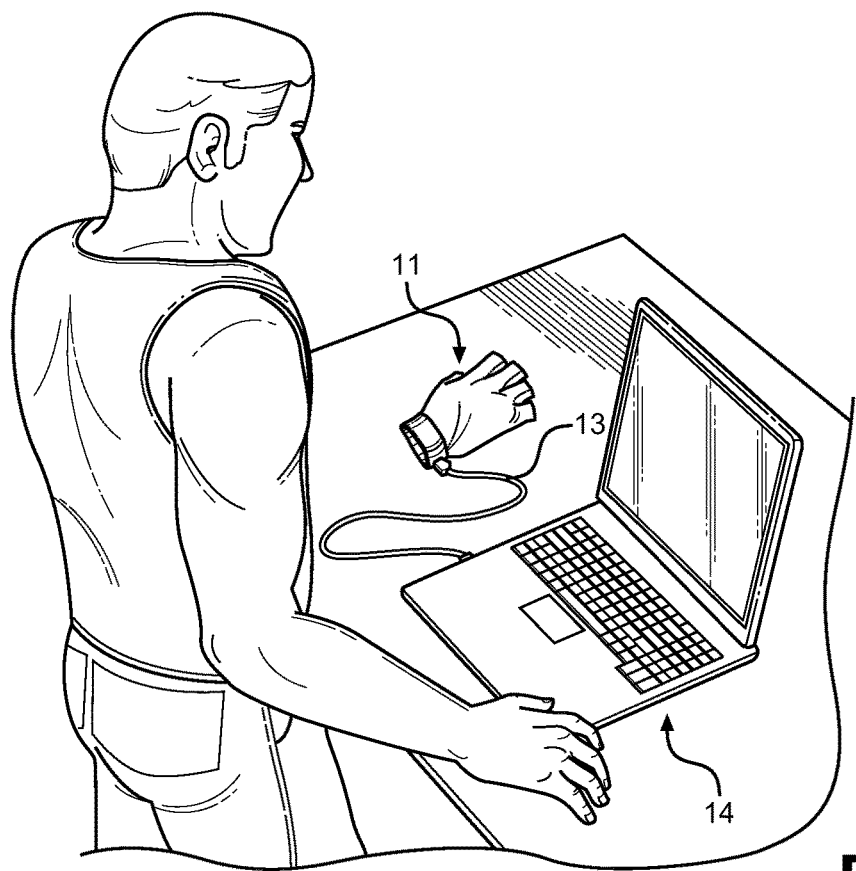
FIG. 2 shows a view of the user transferring collected data to a computer system for analysis and visualization.

Referring now to FIG. 2, there is shown a view of the lifting gloves 11 of the present invention connected to a computer workstation 14 for transferring collected and stored data within the athletic apparel to the computer for analysis and visualization. It is desired that a software application be utilized to collate the data and organize it such that mechanical work and energy requirements from the exercise can be easily studied, as well as forces on the user's body during the activity. The energy output during the activity can be shown and thus the caloric requirements for the workout are known, allowing the user to consume the required calories per day to maintain a proper caloric balance.

Figure 3:
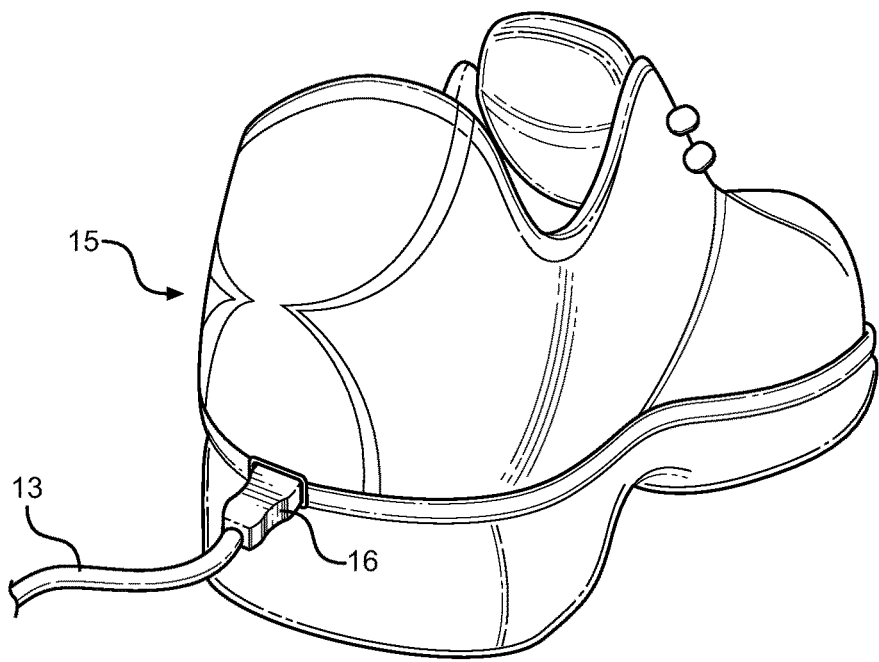
FIG. 3 shows an embodiment of the present invention and method, wherein an athletic shoe is utilized as a means of housing force transducers and for storing collected data during an exercise.

Referring now to FIG. 3, there is shown a view of an embodiment of the present invention that includes a pair of athletic shoes 15 as a means of housing force measuring sensors. The sole of the shoe includes at least one piezoelectric sensor for capture force data, along with an accelerometer for monitoring the position of the shoe during an activity. In a similar fashion as the lifting gloves 11, the shoes 15 include a computer memory for storing the measured data, which is then transferable via a cord 13 and connector 16, or alternatively wireless transfer. As the user runs, presses against the ground or presses against a weight machine, the sensors record force and positional data, which are later utilized to calculate energy output, force on the user's feet and caloric requirements of the activity.

The present invention comprises at least one or a series of sensors within an article of athletic apparel, which are designed to collect force and positional data from those individuals training or exercising such that the user can better assess his or her level of energy expenditure and physical fitness. The sensors may be integrated into weight-lifting gloves and shoes to collect energy expenditure data and inform individuals of their daily caloric requirements given their output level, wherein the user is able to consume sufficient calories for his or her output level during an exercise routine. The device is ideally suited for weight lifters, runners, trainers and professionals required to maintain peak levels of fitness and physical conditioning. The sensors measure the force generated by the individual or to the individual, which is useful knowledge in a wide variety of applications.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An article of fitness for measuring caloric output, comprising:
   a glove including a force transducer and an accelerometer embedded therein;
   the force transducer configured to measure and collect force input data exerted onto a surface of the glove during a physical exercise;
   the accelerometer configured to measure and collect positional and acceleration data of the glove during the physical exercise;

a computer memory embedded within the glove, the computer memory configured to store the collected force input data and positional and acceleration data;
wherein the computer memory is operably connected to a data transfer device, the data transfer device configured to transfer the stored force input data and positional and acceleration data to a computer.

2. The device of claim 1, wherein the computer is configured to calculate an anaerobic caloric requirement for the physical exercise using the transferred force input data and positional and acceleration data.

3. The device of claim 1, wherein the force transducer comprises a piezoelectric force transducer.

4. A method of determining caloric output of a given exercise and maintaining daily caloric balance, comprising the steps of:
utilizing a glove comprising a force transducer and an accelerometer disposed in the glove;
gathering force input data exerted onto a surface area of the glove during a physical exercise via the force transducer;
gathering positional and acceleration data of the glove during the physical exercise via the accelerometer;
storing the force input data and the positional and acceleration data on a computer memory embedded within the glove;
transferring the gathered force input data and positional and acceleration data to a computer for analysis;
calculating energy output during said exercise using the transferred force input data and positional and acceleration data;
determining an anaerobic caloric requirement for the physical exercise using the calculated energy output.

5. The method of claim 4, further comprising the steps of: using the caloric requirement to monitor daily caloric balance.

6. The method of claim 4, further comprising calculating a daily caloric balance remaining for a user in light of the caloric requirement for the physical exercise, wherein the daily caloric balance comprises a number of calories a user is required to consume given the energy output of the user.

7. An article of fitness for measuring caloric output, comprising: a glove including a force transducer and an accelerometer embedded therein;
the force transducer configured to measure and collect force input data exerted onto a surface of the glove during a physical exercise;
the accelerometer configured to measure and collect positional and acceleration data of the glove during the physical exercise;
a computer memory embedded within the glove, the computer memory configured to store the collected force input data and positional and acceleration data;
wherein the computer memory is operably connected to a data transfer device, the data transfer device configured to transfer the stored force input data and positional and acceleration data to a computer;
the computer is configured to calculate an anaerobic caloric requirement for the physical exercise using the transferred force input data and positional and acceleration data.

* * * * *